(12) United States Patent
Seriani

(10) Patent No.: US 11,457,807 B2
(45) Date of Patent: *Oct. 4, 2022

(54) SYSTEM AND METHOD FOR ENABLING CUSTOMERS TO OBTAIN REFRACTION SPECIFICATIONS AND PURCHASE EYEGLASSES OR CONTACT LENSES

(71) Applicant: 20/20 Vision Center LLC, West Palm Beach, FL (US)

(72) Inventor: Joseph S. Seriani, Royal Palm Beach, FL (US)

(73) Assignee: 20/20 VISION CENTER, LLC, Garden City, NY (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/107,077

(22) Filed: Nov. 30, 2020

(65) Prior Publication Data

US 2021/0093197 A1 Apr. 1, 2021

Related U.S. Application Data

(63) Continuation of application No. 14/539,853, filed on Nov. 12, 2014, now Pat. No. 10,874,299, which is a
(Continued)

(51) Int. Cl.
  *A61B 3/18* (2006.01)
  *A61B 3/103* (2006.01)
  (Continued)

(52) U.S. Cl.
  CPC .............. *A61B 3/18* (2013.01); *A61B 3/0025* (2013.01); *A61B 3/0285* (2013.01); *A61B 3/103* (2013.01);
  (Continued)

(58) Field of Classification Search
  CPC ....... A61B 3/18; A61B 3/0025; A61B 3/0285; A61B 3/103; G16H 40/67
  (Continued)

(56) References Cited

U.S. PATENT DOCUMENTS

| | | | |
|---|---|---|---|
| 5,914,772 A * | 6/1999 | Dyer | A61B 3/028 351/222 |
| 2004/0116785 A1* | 6/2004 | Bulat | A61B 5/0002 340/286.07 |
| 2005/0280777 A1* | 12/2005 | Dai | A61B 3/032 351/205 |

FOREIGN PATENT DOCUMENTS

DE  4124056 A1  1/1993
WO  WO-9530367 A1 *  11/1995  ............. A61B 3/028

OTHER PUBLICATIONS

Nottingham Chaplin, P. Kay; Field perceptions of the Vision Initiative for Children's preschool vision screening training model; West Virginia University. ProQuest Dissertations Publishing, 2006. 3225383. (Year: 2006).*

(Continued)

*Primary Examiner* — Hiep V Nguyen
(74) *Attorney, Agent, or Firm* — Bryan Cave Leighton Paisner LLP

(57) ABSTRACT

Systems and methods are provided for obtaining sight screenings, optical prescriptions and fittings for eyeglasses and contact lenses. A system can be self-operated through a voice-activated response system that enables an individual to determine one's own refraction, or can be operated with the assistance of a technician. A plurality of customer diagnostic locations can include digital equipment and optical instruments to conduct the sight screening. The data generated at these locations can be transferred to a remotely located eye doctor who interacts with a customer via a live audio-video connection to assist with interpreting the data, (Continued)

diagnosing the customer and operating the instruments at the locations. The eye doctor diagnoses, consults and authorizes the prescriptions for the customer. The customer's data can be sent to a lens laboratory to enable the fabrication, purchasing, and delivery of eyeglasses or contact lenses.

20 Claims, 3 Drawing Sheets

Related U.S. Application Data continuation-in-part of application No. 13/757,393, filed on Feb. 1, 2013, now abandoned, which is a continuation of application No. 11/707,237, filed on Feb. 16, 2007, now abandoned.

(51) Int. Cl.
*A61B 3/028* (2006.01)
*G02C 13/00* (2006.01)
*G06Q 30/06* (2012.01)
*A61B 3/00* (2006.01)
*G16H 40/67* (2018.01)
*A61B 5/00* (2006.01)

(52) U.S. Cl.
CPC ....... *G02C 13/005* (2013.01); *G06Q 30/0633* (2013.01); *G16H 40/67* (2018.01); *A61B 5/0002* (2013.01)

(58) Field of Classification Search
USPC .............................................................. 705/2
See application file for complete search history.

(56) References Cited

OTHER PUBLICATIONS

Wikipedia, "Eye Exmination," at https://en.wikipedia.org/wiki/Eye_examination dated Jan. 22, 2019.

* cited by examiner

SYSTEM AND METHOD FOR ENABLING CUSTOMERS TO OBTAIN REFRACTION SPECIFICATIONS AND PURCHASE EYEGLASSES OR CONTACT LENSES

CROSS-REFERENCE TO RELATED APPLICATIONS

The present application is a continuation of U.S. patent application Ser. No. 14/539,853 filed on Nov. 12, 2014, which is a continuation-in-part of U.S. patent application Ser. No. 13/757,393 filed on Feb. 1, 2013, which is a continuation of U.S. patent application Ser. No. 11/707,237 filed on Feb. 16, 2007. The contents of the above-identified applications are incorporated by reference in their entireties as if recited in full herein.

FIELD OF THE INVENTION

The present invention pertains to the field of vision corrective devices (e.g., eyeglasses and/or contact lenses), and more particularly, to administering eye examinations over a network with the assistance of a remote practitioner.

BACKGROUND OF THE INVENTION

As the functionality and popularity of the Internet has increased enormously over the years, an emphasis has been placed on enabling customers to purchase medical devices from personal computers (PCs). This certainly applies to the purchasing of eyeglasses over the Internet. There have been numerous technological developments in this area over the years.

For example, U.S. patent application Ser. No. 08/874,269 to Fay ("Fay") discloses a system that displays eyeglass frames to a customer on a personal computer (PC) to demonstrate how they will appear. The system ascertains information about a customer's head, face shape, hair color, skin tone and sex using a PC at an optical retail location. Eyeglass frames are recommended to customers who view, select and/or purchase the frame via the PC. In order to obtain the eyeglass frames, the frames must first be sent to the optical retail location. This system, however, does not provide the lenses with the eyeglass frames. Rather, the opticians are required to send the frames to optical laboratories where the lenses are inserted into the eyeglass frames. The completed pair of eyeglasses is then sent back to the optician's retail location and the customers must then return to the retail location to obtain the eyeglasses. The customers are not able to have a completed pair of eyeglasses sent directly to their homes.

U.S. Pat. No. 5,280,570 to Jordan ("Jordan") is directed to a system that displays how a customer's eyes would appear to another person as a result of wearing glasses with certain specifications (e.g., which demonstrates that the customer's eyes may appear larger or smaller as result of wearing the glasses). Customers may try on various eyeglasses, observe their appearance wearing the eyeglasses, and place orders for the eyeglasses. These systems use information obtained from the customer to limit what models of frames it offers to the customer. This information may be obtained either at a store that the customer visits or on a PC.

The aforementioned systems do not disclose anything with respect to obtaining the actual lens specifications or prescriptions and are of no use in determining the specifications and fit of lenses, nor do they deploy digital imaging or information to concurrently compare visual acuity with previous glasses or specifications. As such, they do not derive a complete means to transact, merchandize and offer for purchase current prescription eyeglasses and contact lenses to a customer either at a convenient location or at a remote PC.

U.S. Pat. No. 5,515,268 to Yoda ("Yoda") discloses a system where a customer selects a product at a store location from a product list stored in a PC at a remote location. In this system, a sensor detects customer size information and transmits it to the remote PC. The remote PC then selects a product of appropriate size and shape and sends an image to the store for display on a monitor. The monitor shows the product superimposed on the customer. This system is not directed to a particular product. It instructs the use of an actuator loop which transfers product information to the customer. Like the prior art systems above, this actuator loop is of no use for fitting eyeglasses or contact lenses to a customer or for determining optical specifications.

U.S. Pat. No. 5,592,248 of Norton et al. ("Norton") utilizes a method to provide a fit for eyeglasses to a customer by taking pictures of the customer at one location and transmitting those pictures to a remote location where the pictures are evaluated to allow an accurate determination of the shape and size of the customer's head for custom making of eyeglass frames. Norton, however, does not teach or show the customer how the customer would appear in alternative or different pairs of eyeglass frames, nor does it derive visual acuity and refractive error to determine the lens specifications.

In all of the aforementioned systems, the customer places an order at a storefront or using a PC after trying on frames. In the disclosures provided by Yoda and Fay, the orders are transmitted to a remote PC and the frames are either ordered at the store front or using a PC. However, none of these systems transmit information to determine lens specifications that may be fit for eyeglass frames or contact lenses. After questioning a customer for information and showing the customer how the frames will appear, the selected eyeglass frames must be sent to opticians who fill the specifications and try to fit eyeglasses using photographs or images of the customers. With regard to actually determining and providing the correct prescription lenses, the references discussed above (e.g., Fay) merely state that frames which are purchased using these prior systems may house prescription lenses. Thus, a major drawback of these systems is that customers must utilize eye doctors outside of these systems (and not part of these systems) to derive an optical prescription and to fill and fit the prescription lenses within the selected frames.

In view of the foregoing, there is a need for enabling a customer to derive and determine their own specifications, refractive error and lens prescriptions for eyeglasses or contact lenses and to obtain signatures from eye doctors to confirm, interpret, and provide specifications for eyeglasses or contact lenses. For example, there is a need for diagnosing and determining current optical prescriptions for specifications from eye doctors, either conveniently located near customers or retail locations or electronically on-line. There is also a need for enabling a remotely located eye doctor to authorize the specifications or prescription such that it is immediately able to be filled by opticians (e.g., who may be conveniently located near the customer or retail locations or electronically on-line) and to allow customers to purchase vision screenings and examinations, refractions, and a completed pair of eyeglasses and/or contact lenses rather than just apparel frames. There is further a need for a system that enables the aforementioned tasks associated with selling, processing, and filling orders for eyeglasses or contact lenses to be performed in a rapid manner (e.g., about a day).

SUMMARY OF THE INVENTION

The present invention pertains to the field of vision corrective devices (e.g., eyeglasses and/or contact lenses). Specifically, the present invention is concerned with determining specifications, visual acuities and refractive errors for determining for optical lenses, as well as determining information and fit for glasses or contact lenses to a customer through obtaining digital images and information of a customer. This data is sent to an eye doctor, or a pre-programmed computerized system, for interpretation, results, and/or electronic signature results. The customer also selects and may purchase the prescription, eyeglasses or contact lenses either through a PC or at a convenient location.

The present invention comprises a means and method for providing customers with their visual acuities, refractive errors, and specifications or prescriptions for eyeglasses and contacts, and the means to use those lens specifications, either simultaneously or at a later time, in conjunction with the selection and purchasing of eyeglasses or contacts at a convenient store location or at a PC elsewhere (e.g., located at the residence of a customer or patient).

The present invention encompasses systems and methods for administering eye examinations over a network. In accordance with certain embodiments, the present invention permits a customer to visit any of a number of possible locations. These locations, which may be referred to as optical diagnostic and retail outlets or customer diagnostic locations, are interfaced to electronically ascertain information about the customer's present glasses specifications, visual acuity, refractive error and/or optical prescription or lens lab specifications. Through use of digital imaging, a complete fit of eyeglasses through selections of frames and lenses is offered, either at the optical diagnostic location, or elsewhere on a PC. Each of these diagnostic locations is connected to remote electronic eye doctors who review, interpret, and authorize sufficient information for purchase and selection of eyeglasses and contacts by the customer. This information is ascertained by integrated, electronic-instrument systems utilizing auto-refractometers, auto-lensometers, auto-phoropters, and other diagnostic optical instruments, that store and send data over a protected server to PCs. The information is sufficient for a customer to purchase refractions and eyeglasses. The fabrication data is then immediately sent to a lab via the Internet which either sends the eyeglasses or contact lenses directly to the customer or to the diagnostic location.

In accordance with the present invention, specifications for prescription lenses are determined accurately and take into account refractive errors separately and independently for each eye, as well as refractive errors for spherical power, cylindrical power, and axis degree determination, all of which is not possible with pre-made or molded prescription lenses in reading eyeglasses. For example, the present invention takes the guess work out of purchasing reading glasses or readers, and provides a more accurate lens and specifications determination so that the customer adapts more comfortably and has better vision. Another novel use of the present invention is that the customer may not have to obtain a complete eye examination from an eye doctor in order to obtain new specifications for lenses for eyeglasses or contact lenses. An eye doctor usually performs about twenty tests or procedures, most of which are medical in nature and used to make medical and eye health diagnoses. Included in these procedures is the one, usually subjective test, called a refraction which primarily determines current or new specifications for eyeglass fabrication. In accordance with the present invention, it is not necessary to go through the entire process of conducting a medical eye examination when the customer wants to purchase new specifications or refraction specifications. This is particularly useful when the customer has broken or lost his eyeglasses and needs to conveniently and quickly purchase new ones.

The present invention utilizes digital data derived from integrating technologically advanced ophthalmic instruments and digital imaging devices. It provides a more efficient method for customers to obtain optical specifications heretofore only available by an examiner who provides refractive results obtained through a traditional, office-visit refraction. It uses a highly efficient system of subjective and objective refractive optical instruments which may be integrated with a voice-activated response system that interacts with the customer to provide a current optical prescription that is precise and accurate. The automated system is more accurate and precise than if the examination had been performed by an experienced clinician. It is virtually a "do-it-yourself" technique for generating and obtaining an accurate optical prescription.

The efficiency, speed, and do-it-yourself refraction aspects of this method are designed to save customers money and time. The present invention provides inexpensive and efficient screenings to determine whether visual loss is merely refractive or due to a medical anomaly, which in that case, the customer is referred to an ophthalmologist who typically does not sell or dispense eyeglasses. With prior art techniques, this process was much costlier and required the customer to visit an optometrist or optician office. Moreover, with these prior systems, there was no interfacing or ability to gather data necessary to determine refractions and provide eyeglasses for immediate purchase either at a convenient retail location or on the Internet.

In addition, the invention comprises an improved and more efficient digital imaging system that allows the customer to select and purchase frames and lenses based on the previous or current optical prescription self-derived as described above. It is a one-stop-shop, never before available or offered to the public in such a time saving and cost saving fashion.

A further object of the present invention is to make it convenient for customers to purchase refractions, eyeglasses, and contact lenses and assist them with information and digital images necessary to make purchase choices either at a diagnostic location or elsewhere on a PC.

The above objects and others not specifically recited may be realized in a specific illustrative embodiment of a system enabling customers to obtain sufficient information to purchase a complete pair of eyeglasses or contact lenses either at a diagnostic location or elsewhere on a PC. In addition, this information can be retrieved and later modified by customers on PCs or at a diagnostic location.

The present invention is unlike any other vision screening scheme. It may be implemented with or without an unskilled onsite technician. It accurately determines whether one may have a suspicious vision disorder, anomaly or disease and is able to provide new prescription eyeglasses in a unique way. There has never been an efficient system utilizing a unique integration of electronic instruments, interfaced in a way to obtain a complete prescription for, and fitting and purchasing of, new eyeglasses in about ten minutes, and an improvement of about five-times more access to those who need vision correction. Prior art systems and methods do not have the ability to improve the sight of nearly 1 billion people worldwide who are legally blind by US standards. The present invention will materially enhance the quality of life of human kind by contributing to the accuracy, accessibility, and affordability of prescription eyeglasses. This system will improve the vision of people who need corrective lenses.

Certain embodiments also relate to a system enabling a customer to obtain a sight screening as well as a fitting and optical prescription for eyeglasses or contact lenses through digital instruments and optical equipment utilized and operated by the customer through a voice-activated response system, an onsite technician/optician who may assist with providing a virtual refraction, and/or an online, remote eye doctor (ophthalmologist or optometrist). The customer is also able to obtain information to purchase eyeglasses or contact lenses from a convenient optical store location or at home through a PC.

In certain of these embodiments, the system comprises: (a) at least one customer diagnostic location that determines a screening for sight and for the optical specifications or prescription using electronic and/or wave-front, refracting ophthalmic instruments. The at least one customer diagnostic location also determines a correct fitting for frames and lenses through an electronic, digital-imager that provides proportionate, to-scale facial, head, eye, and pupil images, and frame and lens color, style, and size choice changes. The customer diagnostic location may also store all related data including customer identification information and ordering information for the purchasing of eyeglasses and contact lenses. Any data associated with the customer or eye examination may made available to the customer or other individual on a CD-ROM or other storage medium; and (b) A remote, on-line eye doctor, who through an interfaced, tele-health system, has means to consult, diagnose, interpret, treat, and transfer health, optical, or medical data and to provide results of sight and vision screening, refractive error, and lens prescription and specifications obtained through digital imaging devices, electronic and/or wave-front auto-lensometer, so that the customer may choose and purchase eyeglasses. In certain embodiments, the system may include a fully automated voice-activated, computerized response self-refracting system which determines reference error and lens prescription with the need for assistance by a technician and/or remote eye doctor. The system interfaces with an auto-refractometer and auto-phoropter instruments to provide data to the remote eye doctor to determine specifications for new prescription eyeglasses. In response to receiving information related to the remote eye doctor's determination, the system may provide the customer with the eye doctor's electronic signature and optical specifications for purchasing prescription optical lenses.

Certain embodiments are implemented without the assistance of an online eye doctor where the customer interacts directly with interfaced auto-refractometer, auto-lensometer, and auto-phoropter instruments through a voice activated system. This system includes an integrated, interfaced computer which utilizes the customer's subjective refractive responses and also the findings of objective auto-phoropter, auto-lensometer, and auto-refractometer instruments in order to derive and provide specifications for previous specifications for eyeglasses, current refractions and/or new specifications for eyeglasses or contact lenses. The customer may also interact with digital imaging devices, with or without an interrogator (e.g., which may comprise onsite technician or automated computer system), in order to choose and purchase eyeglasses and contact lenses, either from a convenient location or elsewhere on a PC.

In certain embodiments, the customer diagnostic location further comprises: (a) an interrogator/technician/optician who assists with gathering data for the remote eye doctor, providing the sight screening results and/or optical prescription with an electronic signature to the customer, digitally imaging the customer for determining an appropriate fitting and for choosing frames and lenses, and gathering customer identification (ID) data for the purchase of eyeglasses and contact lenses; (b) a customer-direct interface with ophthalmic instruments that provides specifications for previous prescription eyeglasses (e.g., an auto-lensometer for the duplication of previous eyeglasses), provides specifications for current or new eyeglasses (e.g., using an auto-phoropter which determines an accurate subjective refraction) utilizing a voice-activated system based upon the customer's responses, and an auto-refractometer for providing specifications for current or new eyeglasses or contact lenses; (c) an interface with an electronic digital imager, electronic and wave-front auto-lensometer and refractometer ophthalmic instruments, and for providing customer ID data and a CD-ROM or other storage device (e.g., that includes information associated with the customer and/or eye examination); and (d) an interface with the remote electronic store providing the customer access through a PC, the results of the sight screening and/or current optical specifications to purchase eyeglasses and contact lenses without having to physically walk into the optical store location.

According to certain embodiments, the optical store further comprises an eyeglasses and contact lens data store for providing optical data, wherein the interrogator/technician has means for providing the results of the sight screening, eyeglass lenses, frames, and contact lens product information, and further, wherein the customer interface is responsive to the optical product information so as to provide said information to the customer through a PC operated by the customer. In certain of these embodiments, the optical store and/or diagnostic location has means for interrogating and receiving eyeglasses and contact lens selection data from the customer and for providing the optical selection data to the remote electronic store, wherein the remote electronic store technician is responsive to said eyeglasses selection data and suggests to the customer structural material, style characteristics, and sizes of eyeglasses in accord with the customer selection data and optical specifications provided by the remote-online eye doctor.

In accordance with certain embodiments, a system, method and computer program product are provided for allowing customers to obtain optical prescriptions for eyeglasses or contact lenses remotely over a network. Optical equipment is configured to perform one or more vision tests. The optical equipment may include at least one auto-refractometer and at least one auto-phoropter. At least a portion of the optical equipment is controlled through an equipment interface coupled between the computing device and the optical equipment. Controlling at least a portion of the optical equipment may include receiving commands over the network to control the optical equipment based on inputs received from the remote practitioner via an equipment controller interface that is presented on a computing device at the remote practitioner's location. User data pertaining to the customer and a request for vision screening is received from a customer through a user interface coupled to the computing device. Objective vision data associated with an objective refraction of at least one eye of the customer is generated using the optical equipment. Subjective vision data associated with a subjective refraction of the at least one eye is generated using the optical equipment and one or more responses received from the customer through the user interface. Vision screening data is sent to a remote practitioner via a network. The vision screening data pertains to one or more of the objective vision data, the subjective vision data, and the user data and enables the remote practitioner to determine a refractive error for the at least one eye. In response to sending the vision screening data, prescription data is received from the remote practitioner via the network. The prescription data includes an optical prescription associated with the at least one eye. The optical prescription is provided to the customer.

In certain embodiments, the user interface comprises a response sensitive voice-activated component adapted to generate audio for output to the customer and to receive voice-based inputs including the one or more responses from the customer. The voice-activated component is configured to utilize the one or more received responses to automatically adjust the optical equipment and to determine a subjective refraction for the customer without assistance from on onsite technician. The voice-activated component outputs questions to the customer and, based on the one or more responses from the customer, determines an appropriate manner of adjusting the optical equipment in order to properly determine the subjective refraction for the customer.

In accordance with certain embodiments, a system, method and computer program product are provided for implementing a fully-automated vision screening system that allows customers to obtain optical prescriptions for eyeglasses or contact lenses without the assistance of a remote practitioner or onsite technician. Optical equipment is configured to perform one or more vision tests. The optical equipment includes at least one auto-refractometer and at least one auto-phoropter. At least a portion of the optical equipment is controlled by the customer through an equipment interface coupled between a computing device and the optical equipment. User data pertaining to the customer and a request for vision screening is received from a customer through a user interface coupled to the computing device. Objective vision data associated with an objective refraction of at least one eye of the customer is generated using the optical equipment. Subjective vision data associated with a subjective refraction of the at least one eye is generated using the optical equipment and one or more responses received from the customer through the user interface. The vision screening data pertaining to one or more of the objective vision data, the subjective vision data, and the user data is analyzed to automatically determine a refractive error for the at least one eye. Prescription data including an optical prescription associated with the at least one eye is determined. The optical prescription is provided to the customer. The user interface may include a response sensitive voice-activated component as described herein.

In certain embodiments, the refractive error for the at least one eye is compared to a portion of the user data that indicates a prior refractive error that was determined for the at least one eye and the computing device determines whether the difference between the refractive error and prior refractive error is within an acceptable range. The acceptable range is based, at least in part, on the date that the prior refractive error was determined. One or more tests associated with generating the refractive error are re-administered to the customer in response to determining that the difference between the refractive error and prior refractive error does not fall within an acceptable range.

These and other features and advantages will become apparent from the following detailed description of illustrative embodiments thereof, which is to be read in connection with the accompanying drawings.

BRIEF DESCRIPTION OF DRAWINGS

The inventive principles are illustrated in the figures of the accompanying drawings which are meant to be exemplary and not limiting, in which like references are intended to refer to like or corresponding parts, and in which.

DETAILED DESCRIPTION OF THE EMBODIMENTS

Figure 1:
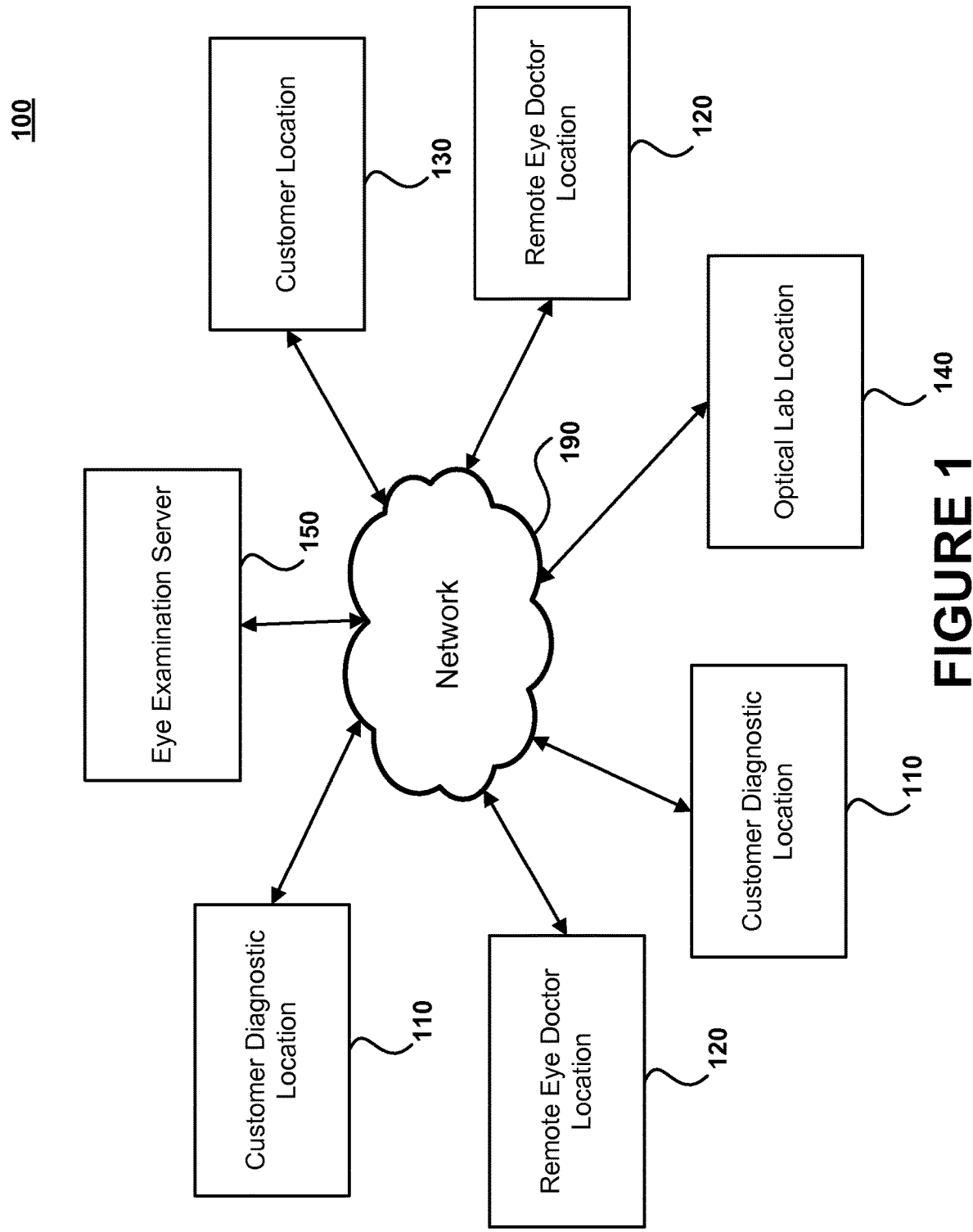
FIG. 1 is a block diagram of an eye examination system in accordance with certain embodiments of the present invention.

In the following description, reference is made to the accompanying drawings that form a part hereof, and in which is shown by way of illustration specific embodiments in which the invention may be practiced. It is to be understood that other embodiments may be utilized and structural changes may be made without departing from the scope of the present invention.

In accordance with certain embodiments of the present invention, systems, methods and computer program products are provided for implementing a remotely assisted vision screening system that allows customers to obtain optical prescriptions for eyeglasses or contact lenses. The vision screening system comprises optical equipment configured to perform one or more vision tests. The optical equipment may include at least one auto-refractometer and at least one auto-phoropter. Other types of equipment may also be utilized (e.g., such as an auto-lensometer and digital imager). At least a portion of the optical equipment may be controlled through an equipment interface coupled between a computing device and the optical equipment. For example, a practitioner, who is located remotely with respect to the customer, may utilize a PC or other computing device to control the optical equipment located at the customer diagnostic location and to administer eye examinations and tests to the customer.

User data may be received from a customer through a user interface provided to the user at the customer diagnostic location. The user interface may be provided via a computing device at the customer diagnostic location. The user data received from the customer may include information associated with the customer and a request for vision screening. The user data may also include account data associated with the customer (e.g., a username, a password, background information, contact information, order information, payment information and shipping information or other information). The user data may further include preexisting vision information associated with the customer (e.g., optical prescriptions, lens specifications, visual acuity information, and refractive error information associated with the customer). The preexisting vision information may be based on prior visits to an eye practitioner and/or prior use of the vision screening system by the customer.

The system may be configured to generate data associated with an objective refraction and subjective refraction of at least one eye of the customer. Objective vision data associated with an objective refraction of at least one eye of the customer may be generated using the optical equipment. In certain embodiments, the objective vision data may include data associated with determining a preexisting lens specification for the at least one eye based on one or more eyeglasses or contact lenses provided by the customer. Subjective vision data associated with a subjective refraction of the at least one eye of the customer may also be generated using the optical equipment and one or more responses received from the customer through the user interface.

Vision screening data is sent to a remote practitioner via a network. The vision screening data may include one or more of the objective vision data, the subjective vision data, and the user data. The vision screening data enables the remote practitioner to determine a refractive error for the at least one eye. In certain embodiments, the vision screening data may also permit the remote practitioner to perform medical diagnoses associated with the customer's eye (e.g., to perform diagnoses related to eye diseases and/or abnormalities). In response, the vision screening data, prescription data and/or medical diagnosis information is received from the remote practitioner via the network. The prescription data may include an optical prescription associated with the at least one eye of the customer. The optical prescription may comprise a current refractive error for the at least one eye and an electronic signature from the remote practitioner authorizing the optical prescription.

The optical prescription may then be provided to the customer. For example, the optical prescription may be provided to the customer by presenting the optical prescription to the customer through the user interface at the customer diagnostic center, e-mailing the optical prescription to the customer, sending the optical prescription to the customer via postal mail, providing access to the prescription via an account that is accessible through a website or by other means. The optical prescription may include a current refractive error for the at least one eye and an electronic signature from the remote practitioner authorizing the optical prescription. In certain embodiments, providing the optical prescription to the customer includes receiving, via the network, a request from the customer to access the optical prescription and sending, via the network, the optical prescription to a remote computing device associated with the customer.

In certain embodiments, the user interface at the customer diagnostic location comprises a response sensitive, voice-activated component adapted to generate audio for output to the customer and to receive audio input from the customer. One or more responses may be received from the customer through the user interface for generating the subjective vision data associated with a subjective refraction test or other test. The one or more responses received from the customer may comprise voice-based inputs received through the response sensitive, voice-activated component. The response sensitive, voice-activated component may enable a customer to provide any input that is relevant to conducting tests associated with determining a refraction of the customer's eye or diagnosing a medical condition associated with the customer's eye. This may be performed without the assistance of a remote practitioner, onsite technician or other individual.

For example, in certain embodiments, the response sensitive, voice-activated component is adapted to output questions to the customer which are relevant for determining a subjective refraction and to receive responses from the customer indicating the customer's answers to the questions. The feedback or answers provided by the customer may be utilized by the voice-activated component (or other component of the system) to determine a subjective refraction for the customer without human assistance (e.g., without the assistance of an onsite technician or remote eye doctor). As the customer provides feedback to the response sensitive voice-activated component, the optical instruments and other equipment may be adjusted to account for the customers' feedback and to properly conduct the tests related to determining the subjective refraction. In alternative embodiments, the process of determining the subjective refraction is performed with the assistance of an onsite technician and/or remote medical practitioner.

In certain embodiments, a refractive error is determined for the customer's eyes and the refractive error is compared to a portion of stored user data that indicates a prior refractive error that was determined for the customer (e.g., that was determined during a prior visit to a customer diagnostic location or a prior visit to a medical practitioner). The screening system determines whether difference between the refractive error and prior refractive error is within an acceptable range. Thus, if the refractive error and prior refractive error differ greatly, this may indicate to the system that one or more of the tests administered to the customer were not performed properly. The acceptable range may be based, at least in part, on the date that the prior refractive error was determined given that the difference between the determined refractive error and the prior refractive error are is likely to be greater over time. If the difference between the determined refractive error and the prior refractive error does not fall within the acceptable range, it may be required that one or more of the tests associated with the vision screening be re-administered to the customer to ensure that the determined refractive error is accurate.

One or more components of the system can store all of the relevant information and data. For example, the user data, objective vision data, subjective vision data, and prescription data may be stored in a storage device of a server, a computing device at the customer diagnostic location and/or a computing device utilized by a remotely located practitioner. The stored information may be retrieved for use during subsequent visits by the customer or for other reasons.

In certain embodiments, the vision screening system further includes digital imaging equipment adapted to determine fitting data associated with the customer. The fitting data may include data indicating pupillary distances, bifocal seg-heights, lens sizes, and frame sizes.

In addition to providing optical prescriptions to customers, the system may further be configured to provide functions associated with fulfilling orders for eyeglasses and contact lenses and transmitting the eyeglasses and contact lenses directly to a customer (e.g., at his or her residence) or to a customer diagnostic location. For example, the system may receive a request from the customer to order eyeglasses or contact lenses. The request may be received from a computing device at the customer diagnostic location and/or from a customer's personal computer. Order data may then be sent, via the network, to a remote optical lens lab. The order data may include data pertaining to one or more of the user data, the prescription data and the fitting data. The order data enables fabrication of the eyeglasses or contact lenses for delivery to the customer.

In certain embodiments, in response to receiving a request from the customer to order eyeglasses or contact lenses, product data associated with one or more optical products available for purchase is provided to the customer. One or more product selections are received from the customer pertaining to the provided product data. The product selections may identify one or more products that the customer desires to purchase. For example, a customer may identify specific contact lenses and/or eyeglass frames that are desired for purchase. The prescription data, fitting data or other data mentioned herein may be used to fabricate the selected products at an optical lab. The fabricated products may then be transmitted directly to the customer or a customer diagnostic location.

The embodiments described in this disclosure can be combined in various ways. Any aspect or feature that is described for one embodiment can be incorporated to any other embodiment mentioned in this disclosure. Moreover, any of the embodiments described herein may be hardware-based, software-based and preferably comprise a mixture of both hardware and software elements. Thus, while the description herein may describe certain embodiments, features or components as being implemented in software or hardware, it should be recognized that any embodiment, feature or component that is described in the present application may be implemented in hardware and/or software. In certain embodiments, particular aspects are implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer-readable medium may include any apparatus that stores, communicates, propagates or transports the program for use by or in connection with the instruction execution system, apparatus, or device. The medium can be a magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Referring now to the drawings in which like numerals represent the same or similar elements and initially to FIG. 1, an eye examination system 100 is disclosed for administering eye examinations to customers over a network. The system 100 is also configured to determine fitting information for eyeglasses and contact lenses, and to facilitate the selecting, ordering and purchasing of eyeglasses and contact lenses.

Customers seeking eye examinations may visit one or more customer diagnostic locations 110 to the obtain eye examinations. The customer diagnostic locations 110 may represent a storefront, kiosk, booth, or location that includes equipment for conducting eye examinations. The eye examinations may relate to vision screenings for obtaining optical prescriptions. In certain embodiments, the eye examinations may also relate to examinations for treating or diagnosing medical conditions related to the customers' eyes. The customer diagnostic locations 110 may include staff or technicians to assist customers with utilizing the equipment and performing eye tests, or the customers may utilize the equipment and perform the eye tests on their own without any onsite assistance.

Medical practitioners located at remote eye doctor locations 120 may assist with providing the eye examinations. The remote eye doctor locations 120 may represent medical offices or facilities, or any other locations that are physically separate from the customer diagnostic locations 110. The medical practitioners located at the remote eye doctor locations 120 may utilize any suitable computer device (e.g., PC, laptop, mobile device, etc.) to communicate with customers located at the customer diagnostic locations 110 in real-time over a network 190 while data (e.g., user data, objective vision data and subjective vision data) pertaining to the eye examinations is being gathered at the customer diagnostic locations 110. Alternatively, the data associated with the eye examinations may be collected at the customer diagnostic locations 110 and then made accessible to the remote practitioners (e.g., via accounts that are accessible on a website provided on the eye examination server 150) at some later point in time. In certain embodiments, video conferencing software may be utilized to enable communication between medical practitioners and the customers. The medical practitioners may also remotely control optical equipment (e.g., auto-refractometers and auto-refractometers) located at the customer diagnostic locations 110 to generate at least a portion of the data pertaining to the eye examinations. This optical equipment may be controlled using user interfaces that are displayed on the computing devices being operated by the remote medical practitioners. In response to manipulating or interacting with the interfaces, commands may be transmitted over the network 190 to permit the medical practitioners to control the optical equipment.

Any data gathered at the customer diagnostic locations 110 may be transmitted over the network 190 to the remote eye doctor locations 120 to enable the practitioners to determine an optical prescription for the customers (and/or to diagnosis or treat the customers' medical conditions). Optical prescriptions may then be transmitted to the patients over the network 190. The optical prescriptions may also be transmitted over the network 190 to one or more optical lab locations 140. The optical lab locations 140 utilize the optical prescriptions to generate or fabricate eyeglass lens or contact lenses. The optical lab locations 140 can send eyeglasses and/or contact lenses directly to the customers or to the customer diagnostic centers 110.

Customers located at customer locations 130 may utilize their own computing devices to access their optical prescription information and to perform other related functions (e.g., setting up user accounts, selecting eyeglass frames, accessing data associated with prior visits and placing orders for eyeglasses and/or contact lenses). The customer locations 130 may represent homes or residences associated with the customers, or other locations where the customers are provided access to computing devices. In certain embodiments, such as those in which customer locations 130 have the necessary optical equipment, the eye examinations may be conducted at the customer locations 130 rather than the customer diagnostic locations 110.

Each of the customer diagnostic locations 110, remote eye doctor locations 120, customer locations 130, and optical lab locations 140 may include one or more computing devices (e.g., a desktop computer, laptop computer, or other type of computing device). The computing devices at these locations, as well as the eye examination server 150, may be equipped with one or more computer storage devices (e.g., RAM, ROM, PROM, SRAM, etc.) and one or more processing devices (e.g., a central processing unit) that are capable of executing computer program instructions. The computer storage devices are preferably a physical, non-transitory medium. The computing devices may further include displays that are capable of rendering interfaces and one or more input devices (e.g., keyboard, microphone, camera, video camera, scanner, joystick, remote control device, etc.). Individuals may manipulate interfaces rendered on the displays using the input devices to communicate with the eye examination server 150 or other component of the system 100.

The customer diagnostic locations 110, remote eye doctor locations 120, customer locations 130, optical lab locations 140 and eye examination server 150 may include equipment and hardware for communicating and exchanging data with each other over the network 190. The network 190 may be any type of network, such as one that includes the Internet, a local area network, a wide area network, an intranet, etc. The computing devices at the various locations, as well as the server 150, may be configured to communicate via wired or wireless links, or a combination of the two.

The eye examination server 150 may facilitate the exchange of information and communications among the computing devices at the various locations 110, 120, 130 and 140. The eye examination server 150 may receive requests from the customer diagnostic locations 110 for establishing connections with remote practitioners. The requests may identify specific practitioners that are desired for conducting the eye examinations or may be requests to connect to any available practitioners that are connected to the system (e.g., any practitioner who is currently logged into their accounts on the server 150 and available to conduct eye examinations). The eye examination server 150 may select practitioners for handling the eye examinations and may establish connections between the customer diagnostic locations 110 and the remote eye doctor locations 120. The connections may allow a live audio-video or video conferencing feed to be established between the customer diagnostic locations 110 and the remote eye doctor locations. In certain embodiments, each of these system locations 110, 120, 130, 140 and 150 may also be configured to communicate directly with one other.

The eye examination server 150 may generally represent any type of computing device that is capable of communicating with other computing devices over the network 190. In some embodiments, the eye examination server 150 comprises one or more mainframe computing devices that execute a web server for communicating with computing devices over the Internet. The storage medium on the eye examination server 150 can store applications or software code that is configured to provide assistance to users in performing tasks related conducting eye examinations. For example, the eye examination server 150 may host a full-service online platform that enables all of the individuals (e.g., customers, medical practitioners, technicians, optical lab workers, etc.) to access and exchange information for conducting the eye examinations and ordering optical products. The eye examination server 150 may perform any function which relates to establishing communications among the individuals using the system 100 (e.g., customers, medical practitioners, technicians, optical lab workers, etc.), facilitating the exchange of information among these individuals, hosting user accounts for these individuals, and providing user-friendly interfaces to enable different functions to be easily performed (e.g., presenting test results to medical practitioners, sending prescriptions to customers, forwarding customer data to optical labs, etc.). The eye examination server 150 may also provide functions that allow for the ordering and purchasing of eyeglasses and contact lenses using the optical prescription information provided to the customers. The eye examination server 150 (or computing devices at the customer diagnostic locations 110) may further be configured to determine fitting information for eyeglasses and/or contact lenses that are purchased by customers. The fitting information may be derived from digital imaging equipment or other instruments at the customer diagnostic locations 110.

It should be noted that the system in FIG. 1 is merely meant to demonstrate an embodiment of an operating environment that can be utilized in conjunction with the present invention and should not be construed as limiting in any manner whatsoever. The particular configuration in FIG. 1 can be altered in numerous ways without departing from the principles herein. For example, it should be noted that the functionality of the eye examination server 150 in FIG. 1 may be carried out by a plurality of servers and/or could be integrated with one or more customer diagnostic locations. Likewise, any number of customer diagnostic locations 110, remote eye doctor locations 120, customer locations 130 and optical lab locations 140 may be utilized with the system and the system may be configured in a variety of different ways (e.g., in a distributed computing environment, cloud-based environment, client-server environment, etc.).

Furthermore, while the disclosure herein may describe the eye examination server 150 as performing certain functions, it should be recognized that some or all of the functionality provided by the server 150 may be performed locally on the computing devices located at the customer diagnostic locations 110, remote eye doctor locations 120, customer locations 130 and/or optical lab locations 140.

Figure 2:
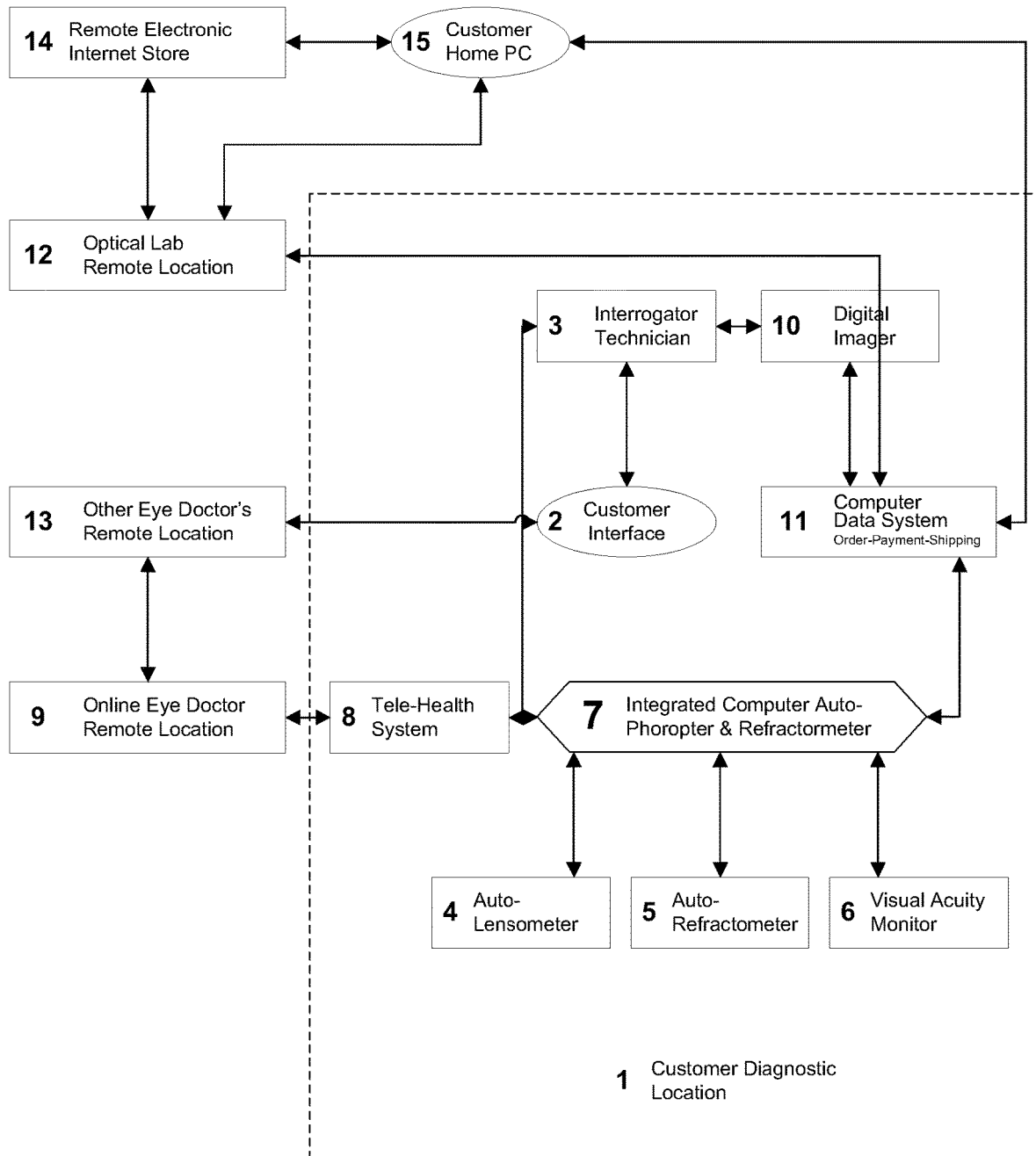
FIG. 2 illustrates a block diagram illustrating the flow of information throughout an eye examination system in accordance with certain embodiments of the present invention.

FIG. 2 is a block diagram illustrating the flow of information throughout an eye examination system in accordance with certain embodiments of the present invention. The figure further demonstrates how a visual acuity screening or refraction and prescription lens specifications may be obtained for eyeglasses. It further demonstrates how to concurrently obtain a fitting for eyeglasses through digital imaging of frames and lenses, as well as how to concurrently purchase eyeglasses and contact lenses at a diagnostic location or elsewhere from a PC (e.g., from a customer location 130) at a later point in time.

The embodiment in FIG. 2 enables a customer to purchase eyeglasses and contact lenses from a home or some other convenient location and includes one or more customer diagnostic locations 1. A customer diagnostic location 1 includes a customer interface 2, an interrogator 3 for determining customer order, shipping, payment information, and technical fitting data (e.g., pupillary distances, bifocal seg-heights, lens and frame styles and sizes), and a tele-health system 8 that provides an interface to a remote, on-line eye doctor 9. In certain embodiments, the interrogator 3 may represent a technician, employee or staff member that assists with conducting eye tests at the customer diagnostic location 1. In other embodiments, the interrogator 3 may represent an automated and/or computer-based system that interacts with the customer 2.

After a customer 2 cooperates with the interrogator 3 (e.g., who may represent a technician/employee/staff member and/or automated computer system that assists with conducting eye tests at the customer diagnostic location 1), the customer data may be interfaced with the on-line eye doctor 9 who determines the lens specifications or prescription data which is sent back to the electronic diagnostic location 2 and stored on its computer data system 11.

The customer 2 may directly interface with an integrated subjective and objective auto-refractometer computer 7 which comprises and controls an auto-lensometer 4, auto-refractometer 5 and auto-phoropter. The computer 7, which is interfaced with these ophthalmic instruments at the diagnostic location 1, has a response sensitive, voice-activation system that provides specifications for current or new lens prescriptions for eyeglasses or contact lenses without having to utilize a remote online electronic eye doctor 9 (or an eye doctor elsewhere, e.g., 13) for conducting an eye examination or determining a refraction.

The interrogator 3 may also assist the customer 2 in performing digital imagery to obtain fitting images 10 in order to allow the customer 2 to browse and store data associated with purchasing frames, lenses, and contact lenses in the computer data system and for ordering, purchasing and shipping 11 the same. The customer 2 may return at a future date to update the data on the ordering system 11 at the customer diagnostic location 1 or order from a PC 15 directly through a remote electronic internet store 14. The interrogator 3 may complete a sales data transaction from the diagnostic location 1, through its computer data system 11 and may send the data to the optical lab location 12 for fabrication. The lab location 12 can either send the eyeglasses or contact lenses directly to the customer or to the diagnostic location 1 for customer pick-up.

At a later time, the customer 2 may purchase eyeglasses or contacts at the diagnostic center 1 or elsewhere from a PC 15. The customer 2 may also purchase an exam or obtain an updated prescription at the diagnostic center 1, through interacting directly with the auto-phoropter system 7 or through the online eye doctor 9. A customer may also purchase an exam or obtain an updated prescription at the place of examination of the remote electronic eye doctor or another eye doctor 13. Thus, the present invention provides a quick and convenient method and system to update and purchase vision care services and eyewear or contact lenses and gives the customer choices and alternatives for choosing healthcare providing eye doctors. The customers may select the eye doctors at the customer diagnostic locations 1. The customer may, at a later time, purchase eyeglasses or contacts at the diagnostic center 1, or at a remote electronic internet store 14, either from a customer diagnostic location 1, or from elsewhere on a PC 15.

In another aspect of the present invention, customers need not visit diagnostic locations at all. If customers have obtained valid and sufficient specifications for eyeglasses and contact lenses from another eye doctor 13, and they enter the corresponding contact and technical data through a PC 15 to a remote internet, electronic, store location 14, the customers may purchase eyeglasses and contact lenses directly and have them shipped either to a convenient store location or to their home or elsewhere. In this aspect, customers may visit a convenient diagnostic location 1 and modify or update their data for future refractions, specifications, and orders for eyeglasses and contact lenses at the computer system 11 for order, payment, and shipping from a convenient location 1 or elsewhere on a PC 15.

The above-described arrangements, interfaces, and systems are only illustrative of the application of the principles of the present invention. In particular, the remote electronic store with its remote electronic eye doctor may be accessed using either the Internet or any other communication line, and the customer may connect to the remote electronic store using a PC from any location that happens to be convenient for the customer—not only the customer's home. Furthermore, the system and method can also be used to purchase other optical accessories and products such as contact lens cases, solutions, frame cases and chains, safety glasses, sunglasses, sports glasses, reading glasses, eyeglass repair kits and warranties.

Figure 3:
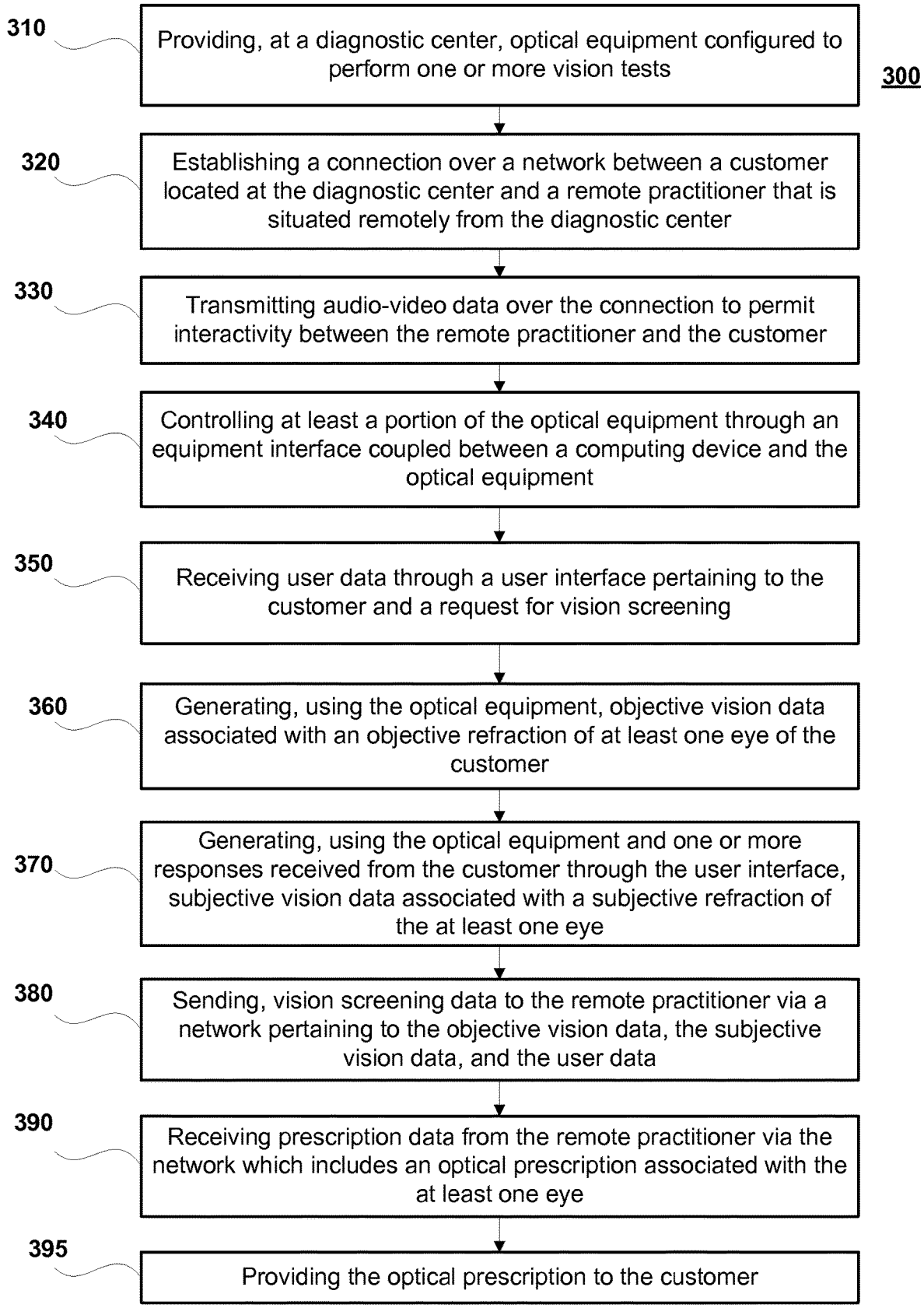
FIG. 3 is a flow chart of a method for providing an eye examination service in accordance with certain embodiments of the present invention.

FIG. 3 is a flow chart of a method 300 for providing an eye examination service in accordance with certain embodiments of the present inventions. Optical equipment configured to perform one or more vision tests is provided at a diagnostic center (step 310). A connection is established over a network between a customer located at the diagnostic center and a remote practitioner that is situated remotely from the diagnostic center (step 320). Audio-video data (or video conferencing data) is transmitted over the connection to permit real-time interactivity between the remote practitioner and the customer (step 330).

At least a portion of the optical equipment is controlled through an equipment interface coupled between a computing device and the optical equipment (step 340). User data pertaining to the customer and a request for vision screening is received through a user interface (step 350). Objective vision data associated with an objective refraction of at least one eye of the customer is generated using the optical equipment (step 360). Subjective vision data associated with a subjective refraction of the at least one eye is generated using the optical equipment and one or more responses received from the customer through the user interface (step 370). Vision screening data pertaining to the objective vision data, the subjective vision data, and the user data is sent to the remote practitioner via the network (step 380). Prescription data is received from the remote practitioner via the network which includes an optical prescription associated with the at least one eye (step 390). The optical prescription is then provided to the customer (step 395).

While there have been shown and described and pointed out various novel features of the invention as applied to particular embodiments thereof, it will be understood that various omissions and substitutions and changes in the form and details of the systems and methods described and illustrated may be made by those skilled in the art without departing from the spirit of the invention. Amongst other things, the steps shown in the methods may be carried out in different orders in many cases where such may be appropriate. Those skilled in the art will recognize, based on the above disclosure and an understanding therefrom of the teachings of the invention, that the particular hardware and devices that are part of the system described herein, and the general functionality provided by and incorporated therein, may vary in different embodiments of the invention. Accordingly, the particular system components shown in the figures are for illustrative purposes to facilitate a full and complete understanding and appreciation of the various aspects and functionality of particular embodiments of the invention as realized in system and method embodiments thereof. Those skilled in the art will appreciate that the invention can be practiced in other than the described embodiments, which are presented for purposes of illustration and not limitation.

What is claimed is:

1. A remotely assisted vision screening system for allowing customers to obtain optical prescriptions for eyeglasses or contact lenses, the system comprising:

a diagnostic center;

optical equipment configured to perform one or more vision tests, the optical equipment being located at the diagnostic center and at least including an auto-phoropter; and at least one computing device that is configured to:

control, during an eye examination for a customer, at least a portion of the optical equipment through an equipment interface that enables the at least one computing device to control the optical equipment;

generate, using the optical equipment, objective vision data associated with at least one eye of the customer;

generate, based on usage of the optical equipment and one or more responses received from the customer, subjective vision data associated with a subjective refraction of the at least one eye;

send vision screening data to a remote individual via a network, the vision screening data at least including the objective vision data and the subjective vision data, wherein the vision screening data enables the remote individual to determine a refractive error for the at least one eye;

receive, in response to sending the vision screening data, prescription data from the remote individual via the network, the prescription data including an optical prescription associated with the at least one eye; and provide the optical prescription to the customer;

wherein the system is configured to:

provide one or more user interfaces to a device operated by the remote individual, the one or more user interfaces permitting the remote individual to perform a remote refraction procedure that enables the customer to obtain the subjective refraction of the at least one eye without assistance from an onsite eye doctor, wherein an audio-video connection between the diagnostic center and remote individual permits audio to be output to the customer and voice-based inputs including the one or more responses to be received from the customer;

receive the voice-based inputs during the eye examination, wherein the at least one computing device is interfaced with the auto-phoropter, the voice-based inputs are utilized by the remote individual to electronically control and adjust the auto-phoropter via the equipment interface during the remote refraction procedure and to determine the subjective refraction for the at least one eye of the customer without assistance from an onsite eye doctor;

provide an interactive audio-video eye examination that enables participation of the remote individual via the audio-video connection, wherein the customer is located at a diagnostic center situated in a first location, the remote individual is located at a second location, the first location and the second location are situated remotely with respect to each other, the remote individual is permitted to permitted to interact with the customer during the interactive audio-video eye examination and to control the auto-phoropter during the remote refraction procedure based on the voice-based inputs including the one or more responses received from the customer;

receive, at the equipment interface during the interactive audio-video eye examination, commands to remotely control or adjust the auto-phoropter during the eye examination;

provide, by the remote individual, the optical prescription to the customer, wherein the optical prescription includes a current refractive error for the at least one eye and an electronic signature from the remote individual authorizing the optical prescription; and provide the optical prescription to the customer, at least in part, by presenting the optical prescription on one or more user interfaces of the at least one computing device.

2. The system of claim 1, wherein controlling at least a portion of the optical equipment includes receiving the commands over the network to control the optical equipment based on inputs received from the remote individual via an equipment controller interface that is presented on the device at the remote individual's location.

3. The system of claim 1, wherein the optical equipment further comprises at least one auto-lensometer and the objective vision data includes data associated with determining a preexisting lens specification for the at least one eye based on eyeglasses or contact lenses associated with the customer.

4. The system of claim 1, wherein the at least one computing device is configured to:

receive, through one or more user interfaces associated with the at least one computing device, user data pertaining to the customer and a request for vision screening, wherein the user data includes account data associated with the customer and the account data is selected from the group consisting of a background information and contact information associated with the customer.

5. The system of claim 4, wherein the user data includes preexisting vision information associated with the customer and the preexisting vision information is selected from the group consisting of a preexisting optical prescription, a preexisting lens specification, preexisting visual acuity information, and preexisting refractive error information.

6. The system of claim 5, wherein the at least one computing device is further configured to store one or more of the user data, the objective vision data, the subjective vision data, and the optical prescription.

7. The system of claim 1, wherein the optical equipment further includes digital imaging equipment that is configured to provide assistance with determining fitting data associated with the customer.

8. The system of claim 1, wherein the system includes one or more servers that provide an online platform accessible via the Internet and the online platform enables communication between the remote individual and the customer.

9. The system of claim 1, wherein the at least one computing device is further configured to transmit audio-video data over the audio-video connection to permit real-time interactivity between the remote individual and the customer.

10. The system of claim 1, wherein controlling at least a portion of the optical equipment includes permitting remote operation of the optical equipment based on the remote individual manipulating an equipment controller interface presented on the device operated by the remote individual.

11. A method for providing a remotely assisted eye examination, the method comprising:

administering an eye examination via an eye examination system, wherein the eye examination system includes a diagnostic center comprising optical equipment configured to perform one or more vision tests and the optical equipment at least includes an auto-phoropter;

wherein administering the eye examination includes:

controlling, during an eye examination for a customer, at least a portion of the optical equipment through an equipment interface that enables at least one computing device to control the optical equipment;

generating, using the optical equipment, objective vision data associated with at least one eye of the customer;

generating, based on usage of the optical equipment and one or more responses received from the customer, subjective vision data associated with a subjective refraction of the at least one eye;

sending vision screening data to a remote individual via a network, the vision screening data at least including the objective vision data and the subjective vision data, wherein the vision screening data enables the remote individual to determine a refractive error for the at least one eye;

receiving, in response to sending the vision screening data, prescription data from the remote individual via the network, the prescription data including an optical prescription associated with the at least one eye; and providing the optical prescription to the customer;

wherein the eye examination system is configured to administer the eye examination, at least in part, by:

providing one or more user interfaces to a device operated by the remote individual, the one or more user interfaces permitting the remote individual to perform a remote refraction procedure that enables the customer to obtain the subjective refraction of the at least one eye without assistance from an onsite eye doctor, wherein an audio-video connection between the diagnostic center and remote individual permits audio to be output to the customer and voice-based inputs including the one or more responses to be received from the customer;

receiving the voice-based inputs during the eye examination, wherein the at least one computing device is interfaced with the auto-phoropter, the voice-based inputs include are utilized by the remote individual to electronically control and adjust the auto-phoropter via the equipment interface during the remote refraction procedure and to determine the subjective refraction for the at least one eye of the customer without assistance from an onsite eye doctor;

providing an interactive audio-video eye examination that enables participation of the remote individual via the audio-video connection, wherein the customer is located at a diagnostic center situated in a first location, the remote individual is located at a second location, the first location and the second location are situated remotely with respect to each other, the remote individual is permitted to permitted to interact with the customer during the interactive audio-video eye examination and to control the auto-phoropter during the remote refraction procedure based on the voice-based inputs including the one or more responses received from the customer;

receiving, at the equipment interface during the interactive audio-video eye examination, commands to remotely control or adjust the auto-phoropter during the eye examination;

providing, by the remote individual, the optical prescription to the customer, wherein the optical prescription includes a current refractive error for the at least one eye and an electronic signature from the remote individual authorizing the optical prescription; and providing the optical prescription to the customer, at least in part, by presenting the optical prescription on one or more user interfaces of the at least one computing device.

12. The method of claim 11, wherein controlling at least a portion of the optical equipment includes receiving the commands over the network to control the optical equipment based on inputs received from the remote individual via an equipment controller interface that is presented on the device at the remote individual's location.

13. The method of claim 11, wherein the optical equipment further comprises at least one auto-lensometer and the objective vision data includes data associated with determining a preexisting lens specification for the at least one eye based on eyeglasses or contact lenses associated with the customer.

14. The method of claim 11, wherein administering the eye examination further comprises:

receiving, through one or more user interfaces associated with the at least one computing device, user data pertaining to the customer and a request for vision screening, wherein the user data includes account data associated with the customer and the account data is selected from the group consisting of a background information and contact information associated with the customer.

15. The method of claim 14, wherein the user data includes preexisting vision information associated with the customer and the preexisting vision information is selected from the group consisting of a preexisting optical prescription, a preexisting lens specification, preexisting visual acuity information, and preexisting refractive error information.

16. The method of claim 15, wherein the at least one computing device is further configured to store one or more of the user data, the objective vision data, the subjective vision data, and the optical prescription.

17. The method of claim 11, wherein the optical equipment further includes digital imaging equipment that is configured to provide assistance with determining fitting data associated with the customer.

18. The method of claim 11, wherein the eye examination system includes one or more servers that provide an online platform accessible via the Internet and the online platform enables communication between the remote individual and the customer.

19. The method of claim 11, wherein the at least one computing device is further configured to transmit audio-video data over the audio-video connection to permit real-time interactivity between the remote individual and the customer.

20. The method of claim 11, wherein controlling at least a portion of the optical equipment includes permitting remote operation of the optical equipment based on the remote individual manipulating an equipment controller interface presented on the device operated by the remote individual.

\* \* \* \* \*